United States Patent
Hagen et al.

[11] Patent Number: 5,641,809
[45] Date of Patent: Jun. 24, 1997

[54] LANOLIN/LANOLIN ACID ESTER SKIN TREATMENT COMPOSITION

[75] Inventors: Resheda Hagen, Oak Ridge, Tenn.; Edward W. Clark, Bradford, England

[73] Assignee: Lansinoh Laboratories, Inc., Oak Ridge, Tenn.

[21] Appl. No.: 162,308

[22] Filed: Dec. 6, 1993

Related U.S. Application Data

[63] Continuation-in-part of Ser. No. 993,019, Dec. 18, 1992, abandoned.

[51] Int. Cl.$^6$ .................................................. A01N 37/00
[52] U.S. Cl. ................................................ 514/558; 424/69
[58] Field of Search ............................... 514/558; 424/69

[56] References Cited

U.S. PATENT DOCUMENTS

| | | | |
|---|---|---|---|
| 3,947,571 | 3/1976 | Murphy | 424/64 |
| 4,784,847 | 11/1988 | Zulliger-Bopp | 424/69 |
| 5,057,497 | 10/1991 | Calam et al. | 514/21 |

*Primary Examiner*—Paul J. Killos
*Attorney, Agent, or Firm*—Sherman and Shalloway

[57] ABSTRACT

A skin treatment composition contains from about 10 to about 90 parts by weight of lanolin and from about 90 to 10 parts by weight of at least one ester of a lanolin acid. Preferably, a lower alkyl ester of lanolin fatty acids is utilized, e.g., isopropyl lanolate. The composition finds particular utility in the prevention or treatment of adverse skin reactions in radiation therapy.

28 Claims, No Drawings

LANOLIN/LANOLIN ACID ESTER SKIN TREATMENT COMPOSITION

CROSS-REFERENCE TO RELATED APPLICATION

This application is a continuation-in-part of application Ser. No. 07/993,019, filed Dec. 18, 1992 now abandoned.

BACKGROUND OF THE INVENTION

1. Field of the Invention

The present invention relates to skin treatment compositions and especially to emollient compositions. More particularly, the present invention relates to compositions comprising lanolin and lanolin acid esters.

2. Description of the Prior Art

Under normal conditions, the water content and vapor pressure of the epidermis are higher than the surrounding air and water evaporates from the surface of the skin. Skin becomes dry due to excessive loss of water from the stratum corneum when exposed to low relative humidities, insufficient hydration from the lower epidermal layers and/or air movement.

Frazier, et al., A Formulary For External Therapy of the Skin, Charles C. Thomas, Springfield, Ill. (1954), pp. 55–69, defined an emollient material as one which prevents or relieves dryness of the skin. Strianse, S. J., "Hand Creams and Lotions" in Sagarin, E., Cosmetics: Science and Technology, Wiley-Interscience, New York (1972), p. 180, defined an emollient as an "agent which, when applied to a dry or inflexible corneum, will effect a softening of that tissue by inducing rehydration".

Skin dryness, and reduced flexibility, of the stratum corneum cannot be corrected by the addition of oily materials, but the skin will become flexible when rehydrated, even in the absence of oily, materials.

It is the decrease in the water content of the stratum corneum which is the main cause of the dry feeling in chapped skin. Inasmuch as the water which diffuses from the dermis to the upper layers is limited in quantity and insufficient to balance the water lost from the skin surface by evaporation, especially in low relative humidities, the skin approaches a certain degree of inflexibility and stiffness. It is here that an emollient finds its maximum use, in serving as an occlusive agent, i.e. a hydrophobic material which reduces or prevents passage of water into or through a film of these substances. The occlusive material acts as a barrier to evaporation of water from the skin surface, and hence permits rehydration of the corneum. In addition, the emollient imparts slip but does not necessarily soften the skin because of its "lubricating" properties.

Barnett, G., "Emollient Creams and Lotions" in Sagarin, E., Cosmetics: Science and Technology, Wiley-Interscience, New York (1972), pp. 34–36, indicates that emollients comprise a long list of materials which may be classified in the following types:

(1) Hydrocarbon oils and waxes;
(2) Silicone oils;
(3) Triglyceride esters;
(4) Acetoglyceride esters;
(5) Ethoxylated glyceride;
(6) Alkyl esters;
(7) Alkenyl esters;
(8) Fatty acids;
(9) Fatty alcohols;
(10) Fatty alcohol ethers;
(11) Ether-esters;
(12) Lanolin and derivatives;
(13) Polyhydric alcohols (polyols) and polyether derivatives;
(14) Polyhydric alcohol (polyol) esters;
(15) Wax esters;
(16) Beeswax derivatives;
(17) Vegetable waxes;
(18) Phospholipids;
(19) Sterols; and
(20) Amides.

Lanolin is the unctuous secretion of the sebaceous glands of sheep which is deposited onto the wool fibers. It softens the fleece and serves to protect the fleece against the elements. It is a wax, not a fat. It is a complex mixture of esters, diesters and hydroxy esters of high molecular weight lanolin alcohols (69 aliphatic alcohols ($C_{12}$–$C_{36}$) and 6 sterols have been identified in lanolin) and high molecular weight lanolin acids (approximately 138 acids ($C_7$–$C_{41}$) have been identified in lanolin). Lanolin is a by-product of the wool-scouring industry.

Wool grease constitutes 10–15% of the weight of sheared wool, depending on the breed of sheep, anatomical area sheared, inner or outer fleece, and season. The average composition of Australian fleeces is 11–16% grease, 6–8% suint (potassium salts of various organic and inorganic acids in the sweat), 10–12% water, 8–19% dirt and 49–61% wool fiber. One hundred pounds of wool yield about 2 to 4 pounds of lanolin. Lanolin is recovered by wool-scouring, followed by separation and purification which may include acid cracking or centrifugal washing, neutralization, removal of soaps, filtration, bleaching and deodorization.

Lanolin is an effective emollient, which by subjective evaluation, effects softening and improvement of dry or rough skin caused by lack of sufficient natural moisture retention. Idson, B. ("What is a moisturizer?", Amer. Perf. Cosm. 87: 33–35 (August, 1972)) reported that lanolin causes the water in the skin to build up to its normal level of 10–30% by retarding, without completely inhibiting, trans-epidermal moisture loss.

A relative quantitative evaluation of the occlusive effect of lanolin and other cosmetic materials on the transpiration of moisture from human skin was made by Powers, et al. ("A study of the effect of cosmetic ingredients, creams and lotions on the rate of moisture loss from the skin", Proc. Sci. Sect. TGA, No. 28, 21–26 (December, 1957)). In particular, lanolin was applied to the inner surface of the forearm (5.0–6.25 mg/cm$^2$, equivalent to a film thickness of 54–68 microns), and was covered with a 28 mm diameter glass desiccator containing silica gel. The uptake of water was determined by weighing the miniature desiccator after specific time intervals. All results were obtained under conditions of zero relative humidity. Lanolin caused a 32% reduction in moisture loss from the skin, indicating a mild occlusive effect for this material as opposed to the extreme barrier effect of petrolatum (48% reduction in moisture loss).

The moisturizing power of lanolin has been demonstrated an quantified by Clark, E. W. ("New concepts of lanolin", Manufacturing Chemist, 61:18–23 (July 1990)). When applied to human stratum corneum, lanolin has been shown to penetrate through the full depth down to the stratum lucidum (Clark, E. W., "Short-term penetration of lanolin into human stratum corneum", J. Soc. Cosmet. Chem., 43-219-227 (July/Aug. 1992)). It has also been shown (in the "New concepts of lanolin" paper referred to above) that lanolin, when in contact with water, will spontaneously emulsify some of that water as a very finely dispersed water-in-oil (w/o) emulsion, with a droplet size less than 0.6 μm, and, conversely, that water emulsified in lanolin can, if the internal/external humidity gradient is favorable, migrate out of the lanolin. In other words, lanolin permits the two-way transport of water and it is believed that lanolin within the stratum corneum can act as a moisture reservoir, absorbing natural epidermal moisture or releasing it depending upon the dryness state of the skin. Lanolin could thus behave in a way analogous to the natural intercellular lipid bilayers in human stratum corneum which hold water and control transepidermal water transport. As previously noted, an adequate moisture content within the stratum corneum is an essential requirement for good skin condition, and applications of lanolin assist in maintaining or restoring the required moisture level.

Lanolin may be used directly on the skin in its 100% form or be incorporated in mixtures or aqueous emulsions which may contain many other ingredients such as emulsifiers, oils, waxes, pigments, etc. Although lanolin exerts its maximum emollience when in the 100% form, the pure substance has a melting point above normal skin temperature and has a rather stiff consistency, which does not make for easy application to the skin, particularly sore skin. Thus, lanolin, per se, is not satisfactory as a skin treatment product because of its high viscosity, tackiness, and high drag property, thereby making it aesthetically unacceptable to consumers and too difficult to spread onto the skin to be widely accepted.

Accordingly, lanolin has historically been used as an auxiliary emulsifier in water-in-oil systems such as the traditional cold creams. In addition to performing as an auxiliary emulsifier, it improves the feel of oil and petrolatum base systems and imparts elegance and a silky smooth texture to the film on the skin. It also modifies the moisture permeability of the extremely occlusive hydrocarbons used in these systems and permits some diffusion of water vapor through the film. This property is related to the fact that lanolin contains a high concentration of hydroxy fatty acid esters of which about 80% are branched. In this respect it resembles human sebum and can in fact duplicate many of the functions of that substance when applied to the skin in cosmetic formulations.

In humans, the branched chain fractions of sebum are at their greatest in the skin of the fetus and diminish with age, becoming much reduced in adults principally because these fatty acids are not derived from metabolism but are by-products of the actual keratinization process, a process which decreases with age. Lanolin can therefore be though of as supplementing these reduced branched chain fatty acids and as a beneficial emollient, softening and superfatting agent. Lanolin finds significant uses in lipstick and eye make-up preparations where its cosolvent and film modifying properties are exploited, almost certainly due to its complex branched ester composition. Typically, it reduces sweating or separation of components in pigmented systems. As might be expected, it is also very effective as a wetting and dispersing agent for pigmented medicaments (zinc oxide, calamine, etc.), and hydrocarbon-based ointments can be easily formulated if relatively large quantities of lanolin are included.

The derivatives of lanolin have also been extensively used as emollients. The derivatives of lanolin can be divided into two classes: physical derivatives, which are the result of physical separation processes such as fractional solvent crystallization; and chemical derivatives, which are the result of chemical modification of lanolin, per se, and hydrolysis of lanolin to fatty acids and fatty alcohols.

U.S. Patent No. 4,960,592 (Hagen, et al., "Lanolin And Lanolin Oil Skin Treatment Composition") seeks to overcome the aforementioned disadvantages of the use of lanolin, per se, by the utilization of a mixture of lanolin and lanolin oil. The lanolin oil, a physical derivative of lanolin (which consists mainly of various esters which cover a wide range of viscosity from mobile liquids to hard waxes), consists of those esters which are naturally liquid at room temperature, separated from whole lanolin by physical means. In particular, by mixing a proportion of lanolin oil with lanolin, the final composition has a reduced melting point, a reduced viscosity and a reduced drag on the skin. Apart from being different in physical consistency, lanolin oil is similar in chemical and general properties to whole lanolin and retains the high emollient power thereof. Although lanolin, and mixtures of lanolin with lanolin oil, are absorbed by the human stratum corneum, the rate of absorption is slow even when assisted by rubbing; and at loadings in excess of 2 mg/cm$^2$ absorption is incomplete and a thin greasy film is left on the skin surface.

As such, a need continues to exist to an emollient composition which is effective and aesthetically acceptable.

SUMMARY OF THE INVENTION

The present invention provides a water-free, skin treatment composition in which the emollient concentration is 100 percent so as to provide maximum effectiveness.

The present invention provides a hypoallergenic skin treatment composition.

The present invention provides a lanolin-based skin treatment composition which is aesthetically acceptable to the consumer.

These and other objects of the invention, as will become apparent hereinafter, have been achieved by the present invention which provides a skin treatment composition consisting essentially of:

(A) from about 50 to about 95% by weight of lanolin;

(B) from about 5 to about 50% by weight of at least one ester of a lanolin acid; and (C) from 0 to about 25% by weight of lanolin oil.

DETAILED DESCRIPTION OF THE INVENTION

Lanolin, as previously noted, is a naturally derived product comprised of a mixture of esters, di-esters and hydroxy esters of high molecular weight lanolin alcohols (Table 1) and lanolin acids (Table 2). It is self-emulsifying, forming stable water-in-oil emulsions, and absorbs up to two or more times its weight of water.

TABLE 1

| LANOLIN ALCOHOLS | |
|---|---|
| Type of Alcohol | No. Identified |
| A. Aliphatic Alcohols | |
| (1) Normal CH$_3$$-$(CH$_2$)$_n$$-$OH <br> (n = 13–33) | 16 |

TABLE 1-continued

LANOLIN ALCOHOLS

| Type of Alcohol | No. Identified |
|---|---|
| (2) Iso $CH_3-CH(-CH_2)_{\overline{n}}OH$ <br> $\quad\quad\quad\quad\quad\;\;|$ <br> $\quad\quad\quad\quad\;\;CH_3$ <br> (n = 11–33) | 11 |
| (3) Anteiso $CH_3-CH_2-CH(-CH_2)_{\overline{n}}OH$ <br> $\quad\quad\quad\quad\quad\quad\quad\;\;|$ <br> $\quad\quad\quad\quad\quad\quad\;\;CH_3$ <br> (n = 13–31) | 11 |
| (4) Normal 1,2-diols <br> $CH_3-(CH_2)_nCH-CH_2$ <br> $\quad\quad\quad\quad\quad\;\;|\quad\;\;|$ <br> $\quad\quad\quad\quad\;OH\;\;OH$ <br> (n = 9–22) | 14 |
| (5) Iso 1,2-diols <br> $CH_3-CH-(CH_2)_n-CH-CH_2$ <br> $\quad\quad\;\;|\quad\quad\quad\quad\quad\;|\quad\;\;|$ <br> $\quad\;CH_3\quad\quad\quad\quad OH\;\;OH$ <br> (n = 9–25) | 9 |
| (6) Anteiso 1,2-diols <br> $CH_3-CH_2-CH-(CH_2)_n-CH-CH_2$ <br> $\quad\quad\quad\quad\quad\;|\quad\quad\quad\quad\quad\;|\quad\;\;|$ <br> $\quad\quad\quad\quad\;CH_3\quad\quad\quad\quad OH\;\;OH$ <br> (n = 9–23) | 8 |
| B. Sterols | |
| (1) Cholesterol | 1 |
| (2) Dihydrocholesterol | 1 |
| C. Trimethyl Sterols | |
| (1) Lanosterol | 1 |
| (2) Dihydrolanosterol | 1 |
| (3) Agnosterol | 1 |
| (4) Dihydroagnosterol | 1 |

TABLE 2

LANOLIN ACIDS

| Type of Acid | No. Identified |
|---|---|
| (1) Normal <br> $CH_3(-CH_2)_{\overline{n}}COOH$ <br> (n = 6–36) | 27 |
| (2) Iso <br> $CH_3-CH-(CH_2)_n-COOH$ <br> $\quad\quad\;\;|$ <br> $\quad\;CH_3$ <br> (n = 4–36) | 17 |
| (3) Anteiso <br> $CH_3-CH_2-CH-(CH_2)_n-COOH$ <br> $\quad\quad\quad\quad\quad\;|$ <br> $\quad\quad\quad\quad CH_3$ <br> (n = 2–36) | 18 |
| (4) Alpha hydroxy normal <br> $CH_3-(CH_2)_n-CH-COOH$ <br> $\quad\quad\quad\quad\quad\quad\;\;|$ <br> $\quad\quad\quad\quad\quad\quad OH$ <br> (n = 7–29) | 23 |
| (5) Alpha hydroxy iso <br> $CH_3-CH-(CH_2)_n-CH-COOH$ <br> $\quad\quad\;\;|\quad\quad\quad\quad\quad\;\;|$ <br> $\quad\;CH_3\quad\quad\quad\quad OH$ <br> (n = 7–29) | 12 |
| (6) Alpha hydroxy anteiso <br> $CH_3-CH_2-CH-(CH_2)_n-CH-COOH$ <br> $\quad\quad\quad\quad\quad\;|\quad\quad\quad\quad\quad\;|$ <br> $\quad\quad\quad\quad\;CH_3\quad\quad\quad\quad OH$ <br> (n = 5–27) | 12 |
| (7) Omega hydroxy normal <br> $HO-CH_2-(CH_2)_n-COOH$ <br> (n = 20–34) | 14 |
| (8) Omega hydroxy iso <br> $HO-CH-CH_2-(CH_2)_n-COOH$ <br> $\quad\quad\;\;|$ <br> $\quad\;CH_3$ <br> (n = 18–32) | 8 |
| (9) Omega hydroxy anteiso <br> $HO-CH_2-CH-(CH_2)_n-COOH$ <br> $\quad\quad\quad\quad\quad\;|$ <br> $\quad\quad\quad\quad CH_3$ <br> (n = 19–31) | 7 |

There are many grades of lanolin available, especially anhydrous lanolins. Most companies use a USP grade of anhydrous lanolin when formulating their products. At this level of refinement, adventitious materials may remain in the lanolin and it will still meet the USP grade requirements. While this poses no threat to the general population, the dermatologically sensitive population may experience an allergic reaction to a cruder grade of lanolin. In this regard, free lanolin alcohols have been identified as the allergen (Takano, et al., Allergens of Lanolin: parts I and II, J. Soc, Cosmet. Chem., 34, 99–125 (March/April, 1983)), especially the diols. Moreover, in combination with detergent residues (residues from the wool scouring process, etc.), the incidence of an allergic reaction increases. For example, Clark et al., Lanolin With Reduced Sensitizing Potential, Contact Dermatitis 1977: 3: 69–74, has shown that as little as 0.1% of detergent may increase significantly the detectable incidence of hypersensitivity, in subjects with a history of lanolin allergy, in the presence of moderate amounts of free alcohols (e.g. about 9%). Higher concentrations of detergents do not result in any further increase. When the free fatty alcohol content is low (e.g. about 2.2%), the addition of detergent has only a slight effect; and when the free fatty alcohol content is high (as in wool alcohols), the addition of detergent has little, if any, observable effect.

Nonetheless, since the incidence of primary specific lanolin allergy amongst the general population has been quantified at 5.5 ±4.2 per million (Clark, E. W., Estimation of the general incidence of specific lanolin allergy, Journal of the Society of Cosmetic Chemists, 26, pp. 323–335 (1975)), and since lanolin, per se, has a lower content of free alcohols than many of the chemical derivatives thereof, the use of lanolin, especially pure anhydrous lanolin, would provide a composition meeting reasonable criteria for hypoallergenicity. Suitable anhydrous lanolins include Clearlan 1650® and Sparklelan 1656® (both products of Quantum Chemical Corporation, a division of Emery). Product specifications for these materials are set forth in Table 3.

TABLE 3

| Specification | Clearlan 1650® | Sparklelan 1656® |
|---|---|---|
| Color (Gardner), Max. | 9 | 12 |
| Free Fatty Acid (USP as oleic), % Max. | 0.56 | 0.56 |
| Moisture (USP), % Max. | 0.25 | 0.25 |
| Melting Range (USP Class II), °C. | 38–44 | 38–44 |
| Ash (USP), % Max. | 0.1 | 0.1 |
| Iodine Value (USP, 0.78–0.82 g sample) | 18–36 | 18–36 |

Alternatively, a very highly refined lanolin may advantageously be utilized such as Anhydrous Lanolin Super Refined (Westbrook SRL®, Westbrook Lanolin Company, England) which meets the following specifications:

TABLE 4

| TEST | LIMITS |
|---|---|
| Melting Point; °C. | 38–44 |
| Water; % w:w | 0.25 max. |
| Residue on Ignition; % w:w | 0.1 max. |
| Water Soluble Oxidisable Substances | Meets USP |
| Iodine Value; % w:w | 18–36 |
| Petrolatum | Meets USP |
| Acidity; mg KOHg$^{-1}$ | 1.12 max. |
| Alkalinity | Meets USP |
| Chloride | Meets USP |
| Water Soluble Acids and Alkalies | Meets USP |
| Ammonia | Meets USP |
| Peroxide Value; me. mg$^{-1}$ | 20 max. |
| Colour; 1/4" Lovibond | 8–14 y |
|  | 0.8–2.0r |
| Free Fatty Alcohols; % w:w | 1.5 max. |
| Detergent Residues; % w:w | 0.05 max. |
| Pesticides Residues | Meets P95 |
| PESTICIDES | P95 LIMIT; ppm |
| Lindane | 0.2 |
| HCH (alpha + beta) | 0.1 |
| HCB | 0.1 |
| Dieldrin + Aldrin | 0.02 |
| Endrin | 0.02 |
| Total DDT etc. | 0.2 |
| Total Heptachlor etc. | 0.1 |
| Total Endosulfan | 0.1 |
| Tecnazene | 0.02 |
| Methoxychlor | 0.1 |
| Dichlofenthion | 0.1 |
| Diazinon | 0.05 |
| Propetamphos | 0.2 |
| Total Chlorfenvinphos | 0.1 |
| Tetrachlorvinphos | 0.1 |
| Malathion | 0.1 |
| Bromophos Ethyl | 0.2 |
| TOTAL | 1.0 |

Lanolin acid esters are produced by the hydrolysis of lanolin, recovery of the lanolin acids therefrom and esterification of the obtained acids. Typically esters with lower alkanols, such as isopropanol or glycerine; with alkanolamines; or with fatty alcohols or sterols are prepared. Such esters are readily available commercially under such trade names as Amerlate® P,W (Amerchol), Crodalan®IPL (Croda USA, Croda Ltd.), Emerest®1723 (Emery), Fancor®IPL (Fanning), Isopropyl Lanolate (Yoshikawa), Lanesta® L, P, S (Westbrook), Lanisolate®(Lanaetex) or Ritasol® (RITA) for isopropyl lanolates; Lanesta® GR (Westbrook) for glyceryl lanolate; Crodamine® (Croda) or Cromeen® (Croda) for alkanolamine esters; cholesteryl lanolate (Yoshikawa); Crodalan®OL (Croda USA, Croda Ltd.) for oleyl lanolate; isocholesteryl lanolate (Yoshikawa); octyl dodecanol lanolate (Yoshikawa); and Super Sterol Esters® (Croda USA, Croda Ltd.) for $C_{10}$–$C_{30}$ carboxylic acid esters of sterols, composed of normal, iso and anteiso lanolin acid esters of predominantly cholesterol and lanosterol. Lower alkanols are preferred for the present invention. By "lower alkanol" is meant any aliphatic of cycloaliphatic alcohol, which may be mono-, di-, tri- or higher-hydric, having up to 6 carbon atoms. Examples include methanol, ethanol, n-propanol, isopropanol, n-butanol, isobutanol, sec-butanol, tert-butanol, pentanol, isopentanol, amyl alcohol (2-methyl-1-butanol), tert-pentanol, cyclopentanol, n-hexanol, cyclohexanol, ethylene glycol, propylene glycol, 1,3-propanediol, 1,2-butanediol, 2,3-butanediol, 1,4-butanediol, 1,2-cyclopentanediol, 1,2-cyclohexanediol, pinacol (2,3-dimethyl-2,3-butanediol), glycerol (1,2,3-propanetriol), and pentaerythritol.

Of the lower alkyl esters of lanolin acids, the isopropyl lanolates have been found to be particularly desirable. In particular, it has now been found that, when isopropyl lanolate is added in minor proportions to either whole lanolin or mixtures of lanolin with lanolin oil, absorption by the stratum corneum is greatly assisted and accelerated. Such mixtures do not leave any detectable surface film and can be absorbed by the skin in as little as 20 seconds. This represents a considerable improvement on lanolin compositions known heretofore.

Isopropyl lanolate, as previously noted, is prepared by hydrolysing the esters which comprise lanolin and then separating the main hydrolysis products, lanolin alcohols and lanolin acids. The latter are then reesterified with isopropanol by known means to yield isopropyl lanolate.

Isopropyl lanolate is a soft buttery solid which melts at about skin temperature, but various segregated fractions are also commercially available, which have lower or higher melting points, such as those known as Lanesta L®, Lanesta SA30® and Lanesta S®. All of these fractions are effective for the present invention. In their pure state, they are completely absorbed by the stratum corneum in 10 to 20 seconds with only gentle rubbing. Not only does isopropyl lanolate itself show rapid absorption by the skin but a new and unexpected discovery is that is has a carrier function which enables it to assist the absorption of other substances by the skin when used as an additive in relatively small proportion. This carrier function is manifested when isopropyl lanolate is added to lanolin and a remarkable finding is that isopropyl lanolate can bring about the complete absorption of several times its own weight of lanolin. At the same time, the mixtures are lower in melting point and show less drag on the skin than either pure lanolin or mixtures of lanolin and lanolin oil. This is an important discovery in relation to the treatment of areas of delicate skin such as the breasts of nursing mothers, babies' buttocks and cases of sore or excessively dry skin. No significant allergenic properties have been attributed to isopropyl lanolate, therefore its admixture does not detract from the essential attributes of hypoallergenic lanolin and hypoallergenic lanolin oil.

The solid, high molecular weight fraction of isopropyl lanolate separated from the total ester mixture by fractional distillation under high vacuum sold under the trade name Lanesta®S has been found to be particularly desirable for preparation of the present compositions. Product specifications for this material are set forth in Table 5.

TABLE 5

| Specification | Value |
| --- | --- |
| Ash, % | 0.1 max |
| Water % | 0.2 max |
| Acid Value, mg KOHg$^{-1}$ | 5.0 max |
| Saponification Value, mg KOHg$^{-1}$ | 115 to 145 |
| Iodine Value (1 gr.), % | 6 to 20 |
| Melting Point, °C. | 30 to 39 |
| Colour, Lovibond 1/4" Cell | |
| Yellow Units (hot) | 10 to 18 |
| Red Units (hot) | 1.0 to 2.5 |

Additionally, the solid condensation product of glycerol and lanolin fatty acids which has been refined by molecular distillation to produce a mixture predominantly composed of di- and tri-esters of lanolin fatty acids sold under the trade name Lanesta®GR has been found to be useful for preparation of the present compositions. Product specifications for this material are set forth in Table 6.

TABLE 6

| Specification | Value |
| --- | --- |
| Ash, % | 0.15 max. |
| Water, % | 0.2 max. |
| Acid Value, mg KOH/g | 5.0 max. |
| Saponification Value, mg KOH/g | 140–180 |
| Slip Point, °C. | 40–55 |
| Appearance | dark, yellow, waxy solid |

The compositions of the present invention may be formed by blending about 10 to about 90% by weight of lanolin with about 90 to about 10% by weight of lanolin acid ester, preferably about 60 to about 90% by weight of lanolin is blended with about 40 to about 10% by weight of lanolin acid ester, most preferably, about 75 to 90% by weight of lanolin is blended with about 25 to 10% by weight of lanolin acid ester.

While it is possible to blend other ingredients, e.g., fragrances, colorants, etc., into the presently contemplated compositions, it is much preferred that the compositions consist solely of lanolin and lanolin acid esters. This avoids the introduction of possible allergens or irritants into the compositions, avoids the possibility of adverse ingredient interactions, and avoids the possibility of additional solubilizing agents being required so as to allow certain ingredients to be added.

Preferably, the present compositions are anhydrous, i.e. have a maximum water content of 0.25% by weight. This is most easily achieved by blending initially anhydrous ingredients under carefully controlled environmental conditions. The substantial exclusion of water from the present compositions provides numerous benefits not the least of which are the avoidance of bacterial growth due to a lack of water, thus enhancing shelf life; and the avoidance of substantial hydrolysis of the esters.

The present compositions may be readily prepared by heating the lanolin, to a temperature above its melting point (38°–44° C.), e.g., 50° C., and then adding the lanolin acid esters, which may have been pre-heated to the same temperature as the lanolin, with mild agitation until a homogenous liquid is formed. The homogenous mass may then be cooled to room temperature (about 20° C.) to form a semi-soft solid having a consistency similar to petrolatum. Preferably, the mixture is first packaged in the desired containers and then allowed to cool.

The present compositions are characterized by ease of spreadability on the skin to form a partially occlusive film. This partially occlusive coating permits rehydration of dry skin by inhibiting transepidermal moisture loss. However, by permitting some passage of water therethrough, it prevents an overhydration of the skin which can cause edema. Additionally, oxygen may pass through the coating thus preventing the propagation of anaerobic bacteria, a factor which may be of importance where the skin is cracked and broken due to excessive dryness and/or scratching by the patient. While the present compositions find their primary utility in the treatment of "dry" skin, they have also been found useful in the treatment of numerous skin lesions such as bed sores and diabetic ulcers.

The present compositions have also been found to be particularly efficacious in the inhibition of adverse skin reactions in patients undergoing radiation therapy and/or the treatment of adverse skin reactions produced in patients undergoing radiation therapy. In each case, twice daily application has been found sufficient to exhibit the therapeutic and/or prophylactic effects of the present compositions.

Additionally, many other uses for the present compositions are possible. In chemotherapy, the compositions can inhibit and/or treat dry skin and cracked, sore lips. Post surgically, the present compositions can be used to reduce the dryness, tautness and itching associated with healing. The compositions can be used to treat an inherited tendency toward dry skin or can be used to treat dry or chapped skin and lips due to over-exposure to the elements (sun, wind, cold, etc.). Moreover, dry, irritated, peeling, cracking or chapping hands and cuticles may also be treated with the present compositions.

The present compositions may be applied at a rate of about 1 gram per 15–25 cm$^2$, and spread by simple rubbing. Of course, greater or lesser amounts may be utilized, although increased amounts do not necessarily produce increased benefits. The present compositions may be applied twice a day, but greater or lesser numbers of applications may be utilized depending on the needs of the patient, as may be influenced by the activities in which the patient engages and/or the bathing frequency of the patient.

Having generally described this invention, a further understanding can be obtained by reference to certain specific examples which are provided herein for purposes of illustration only and are not intended to be limiting unless otherwise specified.

EXAMPLE 1

10 parts by weight of lanolin (Westbrook SRL®) may be melted and blended with 90 parts by weight of isopropyl lanolate (Lanesta S®) to form the composition of the present invention.

EXAMPLE 2

60 parts by weight of lanolin, as in Example 1, may be melted and blended with 40 parts by weight of isopropyl lanolate.

EXAMPLE 3

75 parts by weight of lanolin, as in Example 1, may be melted and blended with 25 parts by weight of isopropyl lanolate.

EXAMPLE 4

90 parts by weight of lanolin, as in Example 1, may be melted and blended with 10 parts by weight of isopropyl lanolate.

EXAMPLE 5

10 parts by weight of lanolin (Westbrook SRL®) may be melted and blended with 90 parts by weight of glyceryl lanolate (Lanesta GR®) to form the composition of the present invention.

EXAMPLE 6

60 parts by weight of lanolin, as in Example 1, may be melted and blended with 40 parts by weight of glyceryl lanolate.

EXAMPLE 7

75 parts by weight of lanolin, as in Example 1, may be melted and blended with 25 parts by weight of glyceryl lanolate.

EXAMPLE 8

90 parts by weight of lanolin, as in Example 1, may be melted and blended with 10 parts by weight of glyceryl lanolate.

EXAMPLES 9–16

A number of different mixtures were made up from lanolin, isopropyl lanolate and, optionally, lanolin oil. 10 mg of each test mixture were placed in the center of a 4 cm² area delineated on the inner forearm of a volunteer subject and gently rubbed in with the tip of the forefinger, using a stopwatch to measure the time required for complete absorption or until no further absorption occurred. In addition, the melting point of each test mixture was determined. The results are summarized in Table 7.

TABLE 7[1]

| COMPO-NENT | EXAMPLE | | | | | | | |
|---|---|---|---|---|---|---|---|---|
| | 9 | 10 | 11 | 12 | 13 | 14 | 15 | 16 |
| Lanolin USP[2] | — | — | — | — | 100 | 90 | 75 | 70 |
| Lanolin SRL[3] | 100 | 85 | 80 | 50 | — | — | — | — |
| Argonol 40[4] | — | — | — | 25 | — | — | — | 15 |
| Lanesta SA30[5] | — | — | 20 | 25 | — | 10 | — | 15 |
| Lanesta S[6] | — | 15 | — | — | — | — | 25 | — |
| TIME (sec.) | 60[7] | 45 | 25 | 20 | 70[7] | 40 | 35 | 35 |
| MELT. PT. (°C.) | 44.0 | 43.0 | 40.5 | 38.0 | 41.3 | 40.0 | 40.7 | 37.3 |

[1] All proportions are percent by weight
[2] Lanolin
[3] Hypoallergenic lanolin (Westbrook)
[4] Isobutylated lanolin oil (Westbrook)
[5] Isopropyl lanolate (Westbrook)
[6] Isopropyl lanolate (Westbrook)
[7] No further absorption In contrast to the two control samples (Examples 9 and 13) of 100% lanolin, the other test mixtures were completely absorbed, and, during absorption, it was noticed that viscosity and drag were much reduced, particularly in the cases of Examples 12 and 16 where the melting points had been reduced to a point only slightly above normal body temperature. Also, the afterfeel on the skin was more pleasant with no residual stickiness.

The following examples are illustrative of the use of the presently contemplated compositions.

EXAMPLE A

Patient: 54 year old—female
Condition: Cancer of hypopharynx
Radiation treatment (site, dose, frequency):
  (i) Tongue—daily dose 180 cGy to total dose of 5040 cGy in 28 treatments
  (ii) Neck—daily dose 180 cGy to total dose of 5040 cGy in 28 treatments
Condition Of Skin Prior To Beginning Of Radiation treatment: Healed surgical scar. No redness.
Skin Treatment: After 1620 cGy, composition of Example 3 applied sparingly, after radiation treatment and at bedtime, daily.
Result: No break in radiation treatment required due to skin problems. Skin is soft and supple. Only mild erythema. No blistering. (Patient was receiving concomitant chemotherapy which increased throat pain but skin reaction was not enhanced.)

EXAMPLE B

Patient: 47 year old—female
Condition: Squamous cell carcinoma, left tonsil, metastasized to left neck
Radiation treatment (site, dose, frequency):
  (i) Bilat. neck (low)/SC (supraclavicular)—daily dose 180 cGy to total dose of 5040 cGy in 28 treatments.
  (ii) Pharynx and upper neck, rt. and lt. lat.—daily dose 180 cGy to total dose of 4500 cGy—then evaluate.
Condition Of Skin Prior To Beginning Of Radiation treatment: Healed surgical scar, otherwise normal appearing skin.
Skin Treatment: After 2700 cGy, composition of Example 3 applied, after radiation treatment and at bedtime, daily.
Result: Completed total dose of 5040 cGy without interruption. Skin remained soft, supple and mildly erythematous but without blisters or break in skin integument.

EXAMPLE C

Patient: 58 year old—female
Condition: Carcinoma of the breast, post lumpectomy, infiltrating ductal carcinoma. (Healed surgical scar, otherwise normal appearing skin.)
Radiation treatment: Treated with an opposed tangential portal and 180 rad a day was given with wedges to the 95% isoline to a total of 5040 rad in 28 treatments over 38 elapsed calendar days.
Skin Treatment: Applied composition of Example 3, daily, after radiation treatment and again at bedtime.
Result: Patient did not experience any adverse reactions. Skin is soft, supple. Mild erythema.

EXAMPLE D

Patient: 53 year old—male
Condition: Squamous cell carcinoma, left posterior nasopharynx.

Radiation treatment: Nasopharynx and upper neck, bi-lat neck—daily dose 180 cGy to total dose of 7020 cGy in 39 treatments.

Skin Treatment: Applied composition of Example 3, daily, after radiation treatment and at bedtime.

Result: Patient's skin had little reaction. Mild redness to lateral neck area and light pink-red to SC (supraclavicular) area. No interruption in treatments.

EXAMPLE E

Patient: 60 year old—female

Condition: Cancer of the tonsil

Radiation treatment: 180 rads/day to a total dose of 6840 rads.

Skin Treatment: Applied composition of Example 3, daily, after radiation treatment and at bedtime.

Result: Patient completed treatment with minimal erythema and no tenderness or pruritis.

EXAMPLE F

Patient: 81 year old—male

Condition: Skin surface carcinoma in the right parotid region

Radiation treatment: 200 rads daily to a total dose of 6600 rads.

Skin Treatment: In week 3, began applying composition of Example 3, daily, after radiation treatment and at bedtime.

Result: Prior to initiation of use, patient had already developed moderate erythema and moist desquamation. By day 3 of use, skin was drying and erythema was mild. By day 5 of use, skin was dry and erythema was minimal. Patient reported comfort level was much improved.

EXAMPLE G

Patient: 53 year old—male

Condition: Head and neck cancer

Radiation treatment: Received 7360 rads to neck

Skin Treatment: Applied composition of Example 3, daily, after radiation treatment and at bedtime.

Result: At end of treatment, patient only had mild erythema.

EXAMPLE H

Patient: 65 year old—female

Condition: Head and neck cancer, poor nutritional health and suffering from a number of chronic illnesses Radiation treatment: Neck and supraclavicular lymph nodes treated to a total of 6600 rads.

Skin Treatment: Applied composition of Example 3, daily, after radiation treatment and at bedtime.

Result: No erythema or desquamation throughout the entire course of radiation treatment.

EXAMPLE I

Patient: 60 year old—female

Condition: Head and neck cancer

Radiation treatment: Received total of 7130 rads to hypopharynx, oropharynx and neck nodes Skin Treatment: Started applying composition of Example 3, daily, after radiation treatment and at bedtime, in week 2, for slight erythema and ear lobe tenderness.

Result: Skin cleared and tenderness resolved within 3 days and patient remained symptom free for skin effect through the end of treatment.

EXAMPLE J

Patient: 41 year old—female

Condition: Infiltrating ductal cancer of the breast

Radiation treatment: Received 200 rad/day to 5000 rads with boost to primary site to 6000 rads for 30 treatments.

Skin Treatment: Applied composition of Example 3, daily, after radiation treatment and at bedtime.

Result: At 2400 rads: mild erythema; and at 6000 rads: moderate erythema with one small area of moist desquamation at skin fold beneath treated breast.

EXAMPLE K

Patient: 68 year old—female

Condition: Recurrent adenocarcinoma of rectal origin within the posterior vaginal wall and soft tissues of the perineum and pelvis. Prior history of B2 adenocarcinoma of the rectum. (Vulva and perineum—pink to red; and numerous small, dry, papillary eruptions localized to labial folds.)

Radiation treatment: Daily radiation to pelvis, vagina and perineum, 6MV, 4 field, 180/fx to 4500 rads; reduce and boost to 5400 rads; and final reduction and boost distal vagina to 6400 rad.

Skin Treatment: Applied composition of Example 3, daily, after radiation treatment and at bedtime.

Result: At 3600 rad—no skin problems. At 4500 rad—minimal vulvar reaction. At 5400 rad—minimal skin reaction. At completion (6400 rad)—minimal skin reaction; skin color pink to red; a few areas of moist desquamation within the labial folds. (Skin rash, described above, at beginning of treatment, is not evident.) Patient reports itching and mild tenderness only—eased upon application of composition.

EXAMPLE L

Patient: 65 year old—female

Condition: Carcinoma of tongue

Radiation treatment: 200 rads/day to tongue for a total of 6600 rads

Skin Treatment: Applied composition of Example 3, daily, after radiation treatment and at bedtime.

Result: No redness. No skin irritation. No desquamation.

EXAMPLE M

Patient: 58 year old—female

Condition: Breast carcinoma. Left breast intact post lumpectomy—axillary node dissection. (Healed scar under arm and above nipple. No skin redness.)

Radiation treatment: Left breast tangent daily 180 rads (4×) to 5040 in 28 fractions. Treatment plan consisted of 15 and 30 degree wedges per site.

Skin Treatment: Applied composition of Example 3, daily, after radiation treatment and at bedtime.

Result: Patient had mild erythema after 15 fractions. Skin had no breakdown. Patient's skin was without pain or discomfort and remained soft and supple with no blistering. Due to appearance of extremely red skin condition, a 12 day break was given with instructions to continue twice daily use of the composition. Patient returned on elapsed day 38. Completed treatment in total of 46 elapsed days. Two weeks after treatment—skin was near normal in appearance.

EXAMPLE N

Ten patients receiving radiation treatment on the breast/chest wall or head/neck treatment areas utilized the composition of Example 3 on one side or half of the treated area and an alternate product on the other. Skin reactions were monitored on a weekly basis. The skin treatment compositions were applied after each daily radiation treatment and at bedtime.

Two patients discontinued the study and switched to the sole use of the composition of Example 3 in order to provide the comfort and healing that they needed.

In all cases, skin reddening during the radiation treatments decreased significantly.

Additionally, patients treated without the composition of Example 3, who obtain varying degrees of desquamation, realize a dramatic improvement in healing within 48 hours after the first application.

Obviously, numerous modifications and variations of the present invention are possible in light of the above teachings. It is therefore to be understood that within the scope of the appended claims, the invention may be practiced otherwise than as specifically described herein.

What is claimed is:

1. A skin treatment composition consisting of
   (A) from about 50 to about 95% by weight of lanolin;
   (B) from about 5 to about 50% by weight of at least one ester of a lanolin acid; and
   (C) from 0 to about 25% by weight of lanolin oil.

2. The skin treatment composition accordingly to claim 1, wherein said lanolin is present in an amount of from about 60 to about 90% by weight and said at least one ester of a lanolin acid is present in an amount of from about 40 to about 10% by weight.

3. The skin treatment composition according to claim 1, wherein said lanolin is present in an amount of from about 75 to about 90% by weight and said at least one ester of a lanolin acid is present in an amount of from about 25 to about 10% by weight.

4. The skin treatment composition according to claim 1, wherein said at least one ester of a lanolin fatty acid is a lower alkyl ester of a mixture of lanolin fatty acids.

5. The skin treatment composition according to claim 4, wherein said lower alkyl ester is an ester of a polyhydric lower alkanol and a mixture of lanolin fatty acids.

6. The skin treatment composition according to claim 5, wherein said polyhydric lower alkanol is glycerine.

7. The skin treatment composition according to claim 6, wherein said at least one lower alkyl ester of a lanolin fatty acid is a fraction of glyceryl esters of lanolin fatty acids which is predominantly di- and tri-esters.

8. The skin treatment composition according to claim 6, wherein said at least one lower alkyl ester of a lanolin fatty acid is a fraction of glyceryl esters of lanolin fatty acids which is predominantly mono-esters.

9. The skin treatment composition according to claim 4, wherein said lower alkyl ester is an ester of a monohydric lower alkanol and a mixture of lanolin fatty acids.

10. The skin treatment composition according to claim 9, wherein said monohydric lower alkanol is isopropanol.

11. The skin treatment composition according to claim 10, wherein said at least one lower alkyl ester of a lanolin fatty acid is a fraction of isopropyl esters of lanolin fatty acids which is liquid.

12. The skin treatment composition according to claim 10, wherein said at least one lower alkyl ester of a lanolin fatty acid is a fraction of isopropyl esters of lanolin fatty acids which is solid.

13. The skin treatment composition according to claim 12, wherein said lanolin is present in an amount of from about 75 to about 90% by weight and said fraction of isopropyl esters of lanolin fatty acids which is solid is present in an amount of from about 25 to about 10% by weight.

14. The skin treatment composition according to claim 12, wherein said lanolin is present in an amount of from about 50 to about 80% by weight, said fraction of isopropyl esters of lanolin fatty acids which is solid is present in an amount from about 25 to about 10% by weight, and said lanolin oil is present in an amount of from about 25 to about 10% by weight.

15. The skin treatment composition according to claim 14, wherein said lanolin is present in an amount of from about 50 to about 70% by weight, said fraction of isopropyl esters of lanolin fatty acids which is solid is present in an amount from about 25 to about 15% by weight, and said lanolin oil is present in an amount of from about 25 to about 15% by weight.

16. The skin treatment composition according to claim 1, wherein said lanolin is present in an amount of from about 50 to about 90% by weight, said at least one ester of a lanolin acid is present in an amount of from about 25 to about 5% by weight, and said lanolin oil is present in an amount of from about 25 to about 5% by weight.

17. The skin treatment composition according to claim 1, wherein said composition is substantially anhydrous.

18. The skin treatment composition according to claim 1, wherein said lanolin is hypoallergenic lanolin.

19. The skin treatment composition according to claim 1, wherein said lanolin oil is hypoallergenic lanolin oil.

20. The skin treatment composition according to claim 1, wherein said composition is hypoallergenic.

21. A method of inhibiting adverse skin reactions in a patient undergoing radiation therapy, comprising:
    applying a therapeutically effective amount of a skin treatment composition to the locus of radiation therapy, at least once after each exposure to radiation,
    said skin treatment composition consisting of
      (A) from about 50 to about 95% by weight of lanolin;
      (B) from about 5 to about 50% by weight of at least one ester of a lanolin acid; and
      (C) from 0 to about 25% by weight of a lanolin oil.

22. The method according to claim 21, wherein a therapeutically effective amount of said skin treatment composition is applied to the locus of radiation therapy after each exposure to radiation and again at bedtime every day during a course of radiation treatment.

23. The method according to claim 21, wherein said lanolin is present in an amount of from about 75 to about 90% by weight, said at least one ester of a lanolin acid being a fraction of isopropyl esters of lanolin fatty acids which is solid, said fraction of isopropyl esters of lanolin fatty acids which is solid is present in an amount of from about 25 to about 10% by weight.

24. The method according to claim 21, wherein said radiation therapy is cancer therapy, and said locus of radiation therapy is an area of the skin exposed to radiation during irradiation of cancer sites.

25. A method of treating adverse skin reactions in a patient undergoing radiation therapy, comprising:

applying a therapeutically effective amount of a skin treatment composition to the locus of adverse skin reaction, said skin treatment composition consisting of
(A) from about 50 to about 95% by weight of lanolin;
(B) from about 5 to about 50% by weight of at least one ester of a lanolin acid; and
(C) from 0 to about 25% by weight of lanolin oil.

26. The method according to claim 25, wherein said lanolin is present in an amount of from about 75 to about 90% by weight, said at least one ester of a lanolin acid being a fraction of isopropyl esters of lanolin fatty acids which is solid, said fraction of isopropyl esters of lanolin fatty acids which is solid is present in an amount of from about 25 to about 10% by weight.

27. A method of moisturizing dry skin, comprising applying a moisturizing effective amount of a skin treatment composition to an area of dry skin on a patient in need of such treatment, said skin treatment composition consisting of
(A) from about 50 to about 95% by weight of lanolin;
(B) from about 5 to about 50% by weight of at least one ester of a lanolin acid; and
(C) from 0 to about 25% by weight of lanolin oil.

28. The method according to claim 27, wherein said lanolin is present in an amount of from about 75 to about 90% by weight and said at least one ester of a lanolin acid is present in an amount of from about 25 to about 10% by weight.

* * * * *